United States Patent [19]
Errico et al.

[11] Patent Number: 5,899,905
[45] Date of Patent: May 4, 1999

[54] EXPANSION LOCKING VERTEBRAL BODY SCREW, STAPLE, AND ROD ASSEMBLY

[75] Inventors: Joseph P. Errico, Far Hills; Thomas J. Errico, Summit; James D. Ralph, Oakland, all of N.J.

[73] Assignee: Third Millennium Engineering LLC, Summit, N.J.

[21] Appl. No.: 09/174,961

[22] Filed: Oct. 19, 1998

[51] Int. Cl.⁶ ................................................. A61B 17/70
[52] U.S. Cl. ................. 606/61; 606/73; 606/75; 606/69
[58] Field of Search .................. 606/60, 61, 69, 606/70, 72, 73, 75

[56] References Cited

U.S. PATENT DOCUMENTS

| | | | |
|---|---|---|---|
| 5,415,659 | 5/1995 | Lee et al. | 606/61 |
| 5,620,443 | 4/1997 | Gertzbein et al. | 606/73 |
| 5,662,652 | 9/1997 | Schafer et al. | 606/73 |
| 5,690,629 | 11/1997 | Asher et al. | 606/75 |
| 5,713,898 | 2/1998 | Stucker et al. | 606/61 |
| 5,810,816 | 9/1998 | Roussouly et al. | 606/61 |

Primary Examiner—Michael Buiz
Assistant Examiner—Daphna Shai
Attorney, Agent, or Firm—Joseph P. Errico, Esq.

[57] ABSTRACT

A rod, screw, rod receiving member, and staple assembly for use in conjunction with anterior or lateral spinal rod implant apparatus includes a vertebral body screw, staple, and rod receiving member which are initially loosely coupled together such that they may each rotate about a common axis. They are held together by virtue of the head of the screw being held within a tapered axial bore of the rod receiving member and the staple being loosely mounted around the rod receiving member. The lower portion of the rod coupling member is expandable by virtue of a series of slots formed in its lower portion. The screw seats within the axial bore of the rod receiving member such that a rod inserted in the channel of the member seats on the head of the screw. With the rod coupling element and staple combination mounted to the screw, it is driven into the vertebral bone. The member is then rotated into position to receive the rod, which seats on the head of the screw. The application of a top locking nut causes the rod to compress against the head of the screw which translates downwardly in the bore, thus expanding the lower portion of the member, and locking the staple and the screw to the member.

7 Claims, 3 Drawing Sheets

EXPANSION LOCKING VERTEBRAL BODY SCREW, STAPLE, AND ROD ASSEMBLY

BACKGROUND OF THE INVENTION

1. Field of the Invention

This invention relates generally to a spinal rod fixation apparatus having an elongate rod, a vertebral body screw, and a stabilizing staple element, and more particularly to a rod, screw and staple assembly having a rotatable screw head which is selectively lockable in combination with the rod and staple to provide enhanced stability and bone holding strength.

2. Description of the Prior Art

The spinal column is highly complex system of bones and connective tissues which houses and protects critical elements of the nervous system and the arterial and venous bodies in close proximity thereto. In spite of these complexities, the spine is a highly flexible structure, capable of a high degree of curvature and twist through a wide range of motion.

Genetic or developmental irregularities, trauma, chronic stress, tumors, and disease, however, can result in spinal pathologies which either limit this range of motion, or which threaten the critical elements of the nervous system housed within the spinal column. A variety of mechanical implant structures have been disclosed in the art which are used during surgical intervention to immobilize segments of the spine which are either unstable or have, in combination, become so irregular that they threaten the continued health of the patient. These assemblies are generally classified as anterior, posterior, or lateral. As the classifications suggest, posterior implants are attached to the back of the spinal column, generally hooking under the lamina and entering into the central canal, attaching to the transverse process, or coupling through the pedicle bone using pedicle screws. Posterior fixation assemblies using such screws are generally used in short sequence immobilization indications, and generally in the larger, lower lumbar bones, for their attending pathologies. Lateral and anterior assemblies, by contrast are coupled to the anterior portion of the spine, which is the sequence of vertebral bodies, and are often used throughout long segments of lumbar and thoracic sequences of vertebrae. A specific pathology which often requires significant surgical intervention along extended numbers of vertebrae is scoliosis. The present invention relates to spinal fixation devices for immobilizing and altering the alignment of the spine over a large number, for example more than three or four, vertebra by means of affixing at least one elongate rod to the sequence of selected vertebral bodies.

Anterior (and/or lateral) "rod assemblies" of the prior art have generally been inserted into the bone either unicortically or bicortically, wherein the shaft of the screw transects (and gains fixation strength as it passes through) one or two exterior layers of the vertebral bone, respectively. Exposing the tip of the screw shaft through the opposing side of the bone's exterior surface does, however, entail a risk inasmuch as important blood vessels, nerve roots, as well as other critical tissues are often in jeopardy of injury through contact with an exposed screw tip. Bicortical fixation, however, provides greatly enhanced strength against pullout; an event in which the screw is pulled free of the bone as its grip inside the vertebra fails to hold.

In order to provide enhanced stability against such pullout events, a staple as shown in FIG. 1, was designed. The basic staple of the prior art comprises a flat metal surface 10 having a hole 12 formed in the center thereof. The corners 14 of the staple 10 are curved downwardly to form four spaced apart spikes. The basic vertebral body screw 20, rod 30 and top locking nut 40 of the prior art are shown in FIG. 2, in conjunction with the staple 10, in an exploded assembly diagram. The screw 20 is inserted through the hole 12 in the staple 10 until the wider top, rod receiving portion 22 of the screw, contacts and seats in the hole 12 of the staple. The wider base, provided by the staple 10, impairs toggling action by the screw within the bone, and is intended to prevent motion which can cause the screw to bone interface from breaking down. The rod 30 is then placed in the rod receiving channel 24 of the screw head 22, and a top locking nut 40 is advanced onto the top of the screw head 22, thereby locking the rod to the screw 20, and by association, to the bone.

In some advanced embodiments of this screw and staple design (not shown), the hole and the bottom of the screw are designed such that the screw may be inserted at a modest angle to the staple, thus permitting stable seating of the screw and staple, despite slight offsets of the screw relative to the bone surface.

These screw and staple assemblies of the prior are, however, do not prevent the most frequent pullout failure mechanism, which is direct vertical force pullout which is caused when the rod itself imparts a sufficient stress against the shaft to cause the screw to back out of the hole. In addition, the ability of the staple to impair toggling of the screw in the bone is limited insofar as the screw and staple are not held together by any specific means, and therefore does not prevent the screw from rotating in the hole and causing microfractures, which can lead to bone failure. Further, the prior art designs limit the ability of the rod receiving head of the screw to be properly aligned with the rod. In many instances, the screw is not fully seated in the hole of the staple because the screw had to be backed out of the hole by the surgeon to align the rod in the rod receiving channel of the head. In such fixed head screw designs, the alignment of the rod receiving channel of the head is not independent of the height of the screw insofar as the rotation of the head causes the threading of the screw to rise up from or dig deeper into the bone. This creates a substantial difficulty for surgeons as they try to seat the rod properly into the screw head while simultaneously having the screw head seat in the hole in the staple.

It is, therefore, the principal object of the present invention to provide a vertebral body screw, rod, and staple assembly which provides enhanced stability and pullout protection.

In addition, it is an object of the present invention to provide such an assembly which includes a stable locking of the staple to the screw so that the screw head can be positioned in the ideal orientation without risking the union of the screw and staple.

It is a related object of the present invention to introduce a screw having a head which may be independently rotated relative to the shaft of the screw, but which may be securely locked in the desired orientation when combined with the screw and staple.

Accordingly it is also an object of the present invention to provide an assembly in which the staple and screw are lockably coupled together upon completion of the implantation It is also a principal object of the present invention to provide a reliable, durable, and efficient, long term fixation assembly for spine stabilization.

Other objects of the present invention not explicitly stated will be set forth and will be more clearly understood in conjunction with the descriptions of the preferred embodiments disclosed hereafter.

SUMMARY OF THE INVENTION

The preceding objects of the invention are achieved by the present invention which is a vertebral body staple, screw and rod assembly, having enhanced stability and pullout strength, in which the staple, the rod and the screw may be locked together to form a reliable fixation to the vertebral bone. More particularly, the assembly of the present invention comprises a vertebral body screw having a shaft and head portion and a rod receiving member which is rotationally mounted thereto. The rod receiving member comprises an upper portion and a lower portion, and an axial bore extending through the center of the body. The upper portion includes a channel for receiving a rod transverse to the axis of the member. The lower portion includes a series of vertical slots formed therein which permit the lower portion to radially expand. The lower portion further includes a pair of spaced apart exterior outwardly extending ring flanges which define therebetween a circumferential recess (also including the vertical slots). The bore includes an axial taper at the lower end thereof such that the forcible insertion of a correspondingly tapered body will cause the lower portion of the body to expand. The head of the screw is rounded and is designed to fit inside the bore in the lower portion of the rod receiving member, with the top of the screw initially seating above the lowermost surface of the rod receiving channel. In the preferred embodiment, the head comprises a frustoconical section. The head of the screw is initially loosely or rigidly maintained in the axial bore by virtue of the fact that the head is larger than the bottom of the bore. More specifically, the tapered exterior of thy screw head and the tapered interior surface of the bore nest together. In the initial state, the rod receiving member floats on the head in such a way that the head may be selectively rotated independently from the shaft portion of the screw. The present invention also includes a vertebral body staple which seats around the lower portion of the rod receiving member, between the flanges, in the recess, and engages the vertebral bone. The insertion of a rod into the channel and onto the head of the screw, followed by the locking of the rod in the channel by means of a nut or set screw, causes the rod to compress the head of the screw into the tapered bottom of the bore, thus causing an expanding force to be applied to the lower portion of the rod receiving member, which causes the member to expand and lock to the staple. Thus, the locking of the rod in the channel simultaneously secures the entire assembly in a rigid position.

Referring specifically to the vertebral body screw of the present invention, the screw comprises a shaft and a head. The shaft portion of the screw is designed to be inserted into the vertebral bone, and to firmly anchor the screw to the bone. This fixation is generally enhanced by the shaft including a threading which engages the bone material along its length and prevents axial translation of the shaft along the length of the hole in the bone into which it has been advanced. The head of the screw is rounded, and, as stated above, is preferably a frustoconical section. More particularly, the head of the screw may curvately or linearly tapered in the axial direction, but should comprise a circular transverse cross section, such that when the head is retained in a similarly shaped volume of the rod receiving member (as more fully described hereinbelow), the shaft and the head may rotate independently from the rod receiving member.

The rod receiving member of the assembly includes an upper portion and a lower portion. An axial bore extends through the member from the upper portion through an opening in the lower portion. The bore is tapered inwardly at the bottom of the member, and the lower portion of the member includes vertical slots which permit the member to expand and contract upon the application of a corresponding force thereagainst. More specifically, tapered bottom of the bore is designed to receive therein the head of the screw and permit the screw to spin independently from the rod receiving member. The forcible advancement of the screw head deeper into the bore causes the sidewalls of the bore to expand outward.

The exterior surface of the lower portion also includes a pair of circumferential flange features, which define therebetween a circumferential recess. This recess has a diameter which expands and contracts in accordance with the above mentioned application of force against the inner surface of the bore. The use and function of this expanding feature by the application of pressure against the inner surface of the bore shall be explained in greater detail with respect to the assembly of the screw, rod receiving member, and the staple.

The upper portion of the rod receiving member comprises a channel for receiving a rod, which channel may alternatively be formed vertically, descending down from the top of the member, or laterally, coming in from the side of the member. More particularly, both types of rod receiving channel admit the rod into the member such that the rod extends perpendicularly to the overall vertical axis of the member, but in the first instance (the vertical channel), the channel is formed between two upright extending arms, and in the second (the lateral channel), the channel is formed in the side of the member. In each embodiment, the upper portion of the member (either the upper portion of the upright extending arms or the portion of the member directly above the lateral channel) includes a threading for receiving thereon a top locking nut, or other means for securing a rod within the channel. In either embodiment, when it is initially inserted into the bore, the head of the screw is designed to seat above the lowermost surface of the channel such that the insertion of a rod into the channel would cause the rod to seat against the head of the screw, and not against the lowermost surface of the channel.

The vertebral body staple comprises a member having a flat portion and a plurality of downwardly directed protuberances, generally shaped like spikes or barbs, which extend perpendicularly to the plane formed by the flat portion. The flat portion further includes a hole formed in the center thereof. The hole in the staple has a diameter which is approximately equivalent to the undeflected diameter of the circumferential recess in the lower exterior of the rod receiving member. The staple is thereby mounted to the rod receiving member by radially compressing the lower portion of the member into the hole in the staple until the lower of the two flanges passes through the hole, such that the staple is axially prevented from movement, but the two elements are able to rotate about one another.

The shaft of the screw is inserted through the bore of the rod receiving member, once the staple has been mounted to the member, until the taper of the exterior of the head engages the taper of the interior of the bore. In this initial disposition, the three elements are loosely coupled and may rotate freely and independently about a common axis (the elongate axis of the screw). The locking of a rod in the rod receiving channel, by means of a nut or set screw(engaging the locking means of the upper portion of the rod receiving member) causes the rod to compress against the head of the screw, which applies an expanding force against the inner surface of the bore, thus expanding the lower portion of the member and locking the staple to the member and the rod in the bore.

The surgical assembly of the present invention is provided as follows. First, the vertebral body surfaces are exposed and prepared to receive the screws (one at each bone). The staple and the rod receiving member are assembled by inserting the lower portion of the member into the hole in the staple until the staple seats in the circumferential recess of the member. The screw is then advanced into the bore until the head of the screw seats against the tapered interior surface of the bore. The screws are then advanced into the bones at the appropriate angles and to the desired height, and the staples are inserted into the bone, as well.

Once the screw and staple have been inserted into the bone, the rod receiving member is rotated into the appropriate alignment to receive the rod. The rod is then placed into each of the channels of the members, extending along the length of the spinal sequence which is to be immobilized. The rod seats against the head of the screw. The locking means, for example a locking nut, is then advanced onto the engaging means of each of the rod receiving members to secure the rod in the channels. The advancement of the rod into the channel by the locking nut, or other such means, causes the head of the screw to be forcibly advanced into the tapered bore of the rod receiving member. The expansion of the lower portion of the rod receiving member causes the exterior surface of the member to compression lock to the staple, and simultaneously, for the head of the screw to be locked in the bore (i.e. prevented from any further rotation). The compressive force of the nut against the rod, the rod against the screw, the screw against the walls of the axial bore of the rod receiving member, and the exterior walls of the rod receiving member against the staple, firmly locks the assembly together and to the vertebral bone.

DETAILED DESCRIPTION OF THE PREFERRED EMBODIMENT

While the present invention will be described more fully hereinafter with reference to the accompanying drawings, in which particular embodiments and methods of implantation are shown, it is to be understood at the outset that persons skilled in the art may modify the invention herein described while achieving the functions and results of this invention. Accordingly, the descriptions which follow are to be understood as illustrative and exemplary of specific structures, aspects and features within the broad scope of the present invention and not as limiting of such broad scope.

Figure 1:
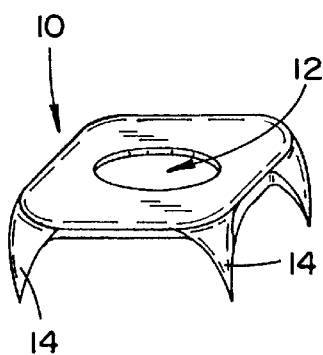
FIG. 1 is a side perspective view of a vertebral body staple of the prior art.
Figure 2:
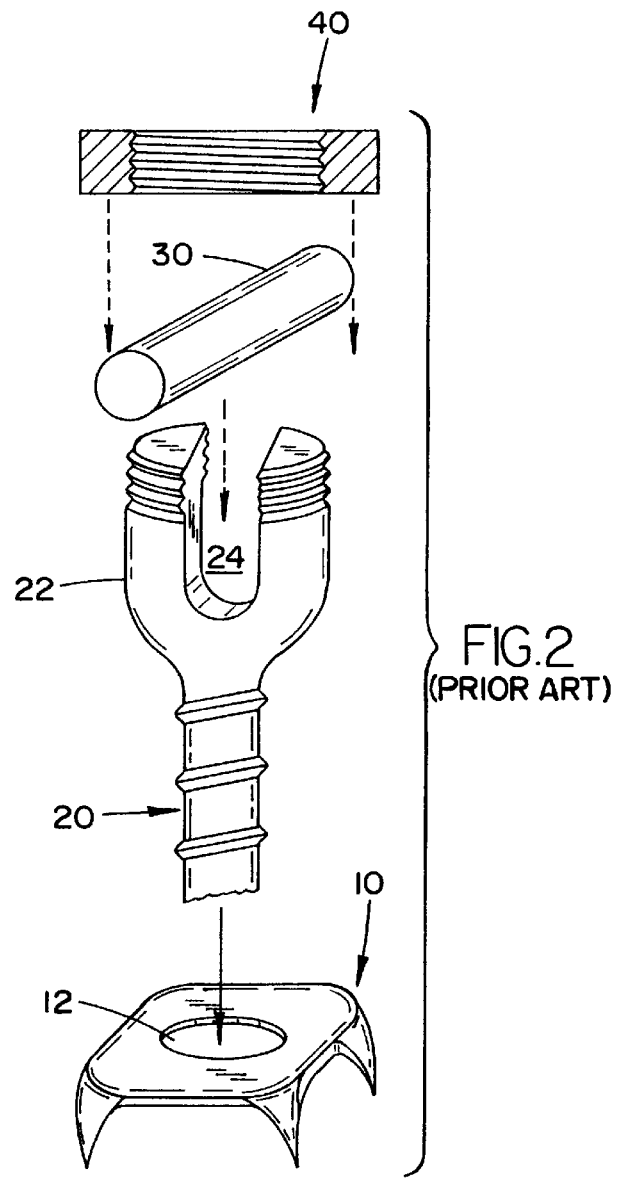
FIG. 2 is an exploded assembly view of a staple, vertebral body screw, rod and top locking nut of the prior art.
Figure 3:
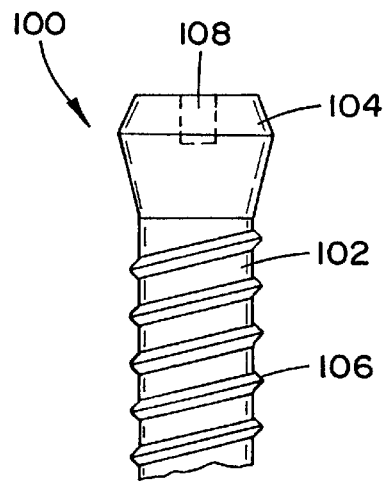
FIG. 3 is a side view of a vertebral body screw which is an aspect of the present invention.

Referring now to FIG. 3, a side view of a vertebral body screw 100 of the present invention, comprising a shaft and a rod coupling head, is shown. The screw 100 comprises a shaft 102, which is threaded, and a head portion 104 having a frustoconical shape. The threading 106 of the shaft 102 is preferably of the type which is suited for high engagement with bone materials, as are well known in the art. It shall be understood that a variety of shaft designs are interchangeable with the present design. The specific choice of shaft features, such as thread pitch, shaft diameter to thread diameter ratio, and overall shaft shape, should be made be the physician with respect to the conditions of the individual patient's bone, however, this invention is compatible with a wide variety of shaft designs.

The head 104 of the screw 100 is round, and, as stated above, is preferably a frustoconical section. A recess 108 is formed in the top of the head 104 so that the screw may be engaged by a torque applying instrument, and thereby be advanced into the vertebral bone. While it shall be understood that the head may curvately or linearly tapered in the axial direction, it should comprise a circular transverse cross section, such that when the head is retained in a similarly shaped bore of the rod receiving member (as more fully described hereinbelow with reference to FIG. 4), the shaft and the head may rotate independently from the rod receiving member.

Figure 4:
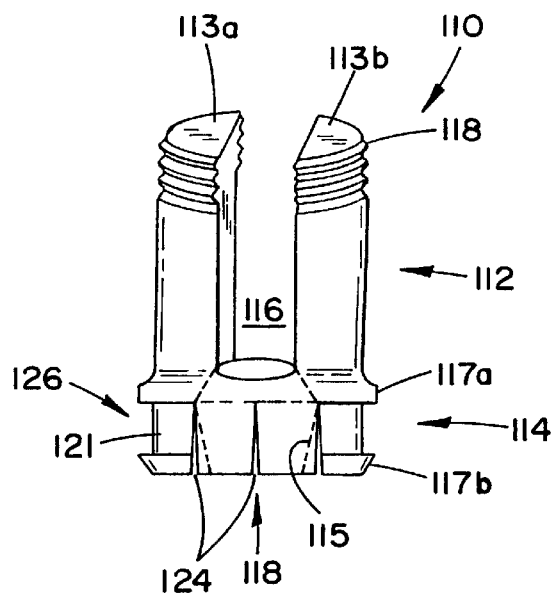
FIG. 4 is a side view of a rod receiving member which is an aspect of the present invention, in which interior features of the member are also shown.

Referring now to FIG. 4, the rod receiving member 110 of the present invention is provided in a side perspective view. The member 110 may be conceptually divided into an upper and lower portions 112 and 114, respectively. The upper portion 112 of the member comprises a pair of upwardly extending arms 113a, 113b which define therebetween a rod receiving channel 116. The uppermost exterior surfaces of the upwardly extending members 113a, 113b include a threading 118 which is ideally suited for receiving a locking nut (as set forth more particularly with respect to FIG. 6). In alternative designs (not shown), which were introduced above, it is possible to design the rod receiving channel 116 into the side of the upper portion 112, however, the preferred embodiment includes the rod receiving channel 116 in a vertical alignment.

The upper and lower portions 112 and 114 of the rod receiving member 110 comprise a cylindrical bore 111 extending through the body. The bore 111 is tapered at the bottom thereof such that the inner surface of the bore forms a frustoconical bearing surface 115 against which the head 104 of the screw 100 may rest. The lower portion 114 of the member 110 further comprises a series of vertical slots 124 formed therein which permit the lower portion to expand and contract radially upon the application of a force, such as a force applied to the bearing surface 115.

The exterior surface 126 of the lower portion 114 also comprises a pair of circumferential flanges 117a, 117b which define therebetween an annular recess 119. The lower flange 117b preferably includes a tapered conformation such that the lowermost portion of the member also comprises a bearing surface 121 against which a force may be applied to cause the slots 124 to narrow, and thus for the lower portion of the member 110 to contract.

Figure 5:
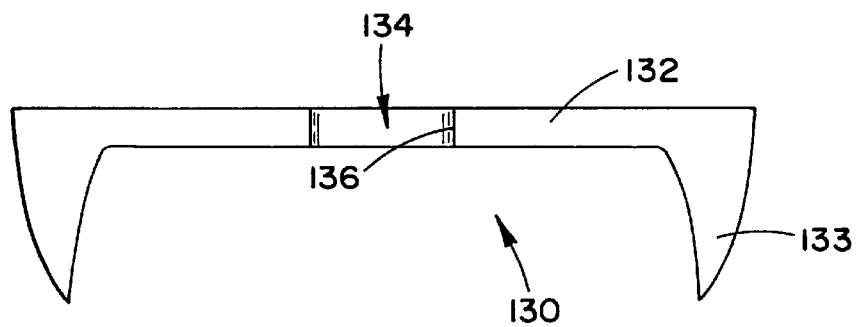
FIG. 5 is a side cross-sectional view of a vertebral body staple which is an aspect of the present invention.

Referring now also to FIG. 5, the vertebral body staple 130 of the present invention is provided in a side cross section view. The staple 130 includes a flat surface 132 and a plurality of downwardly directed barbs 133, disposed at the lateral edges of the flat portion 132. The barbs 133, which are intended to be inserted into the vertebral bone surface to provide fixation of the staple to the bone, extend perpendicularly downward from the plane formed by the flat portion 132. The flat portion 132 further includes a hole 134 formed in the center thereof. The hole 134 has a cylindrical rim 136 which has a diameter approximately equivalent to the undeflected diameter of the annular recess 119. The outer bearing surface 121 of the rod receiving member is designed to compressibly advance through the hole 134 in the staple until the member snaps into position having the cylindrical rim 136 of the staple mounted around the member.

Figure 6:
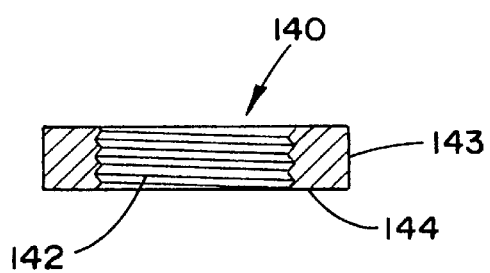
FIG. 6 is a side cross-section view of a top locking nut which is an aspect of the present invention.

Referring now to FIG. 6, a top locking nut 140 of the present invention is provided in a side cross section view. The nut 140 comprises a standard threaded nut design, having an interior threading 142 which is matable and advanceable along the exterior threading 118 of the upper portion 112 of the rod receiving member 110. The exterior surface 143 of the nut 140 is ideally suited for engagement and advancement along this threading 118 by means of a standard torque applying instrument, such as having a series of flats for engaging a wrench or socket. The lower surface 144 of the nut 140 is flat, thus providing maximal surface area over which the downward locking force applied by the nut may be borne.

Figure 7:
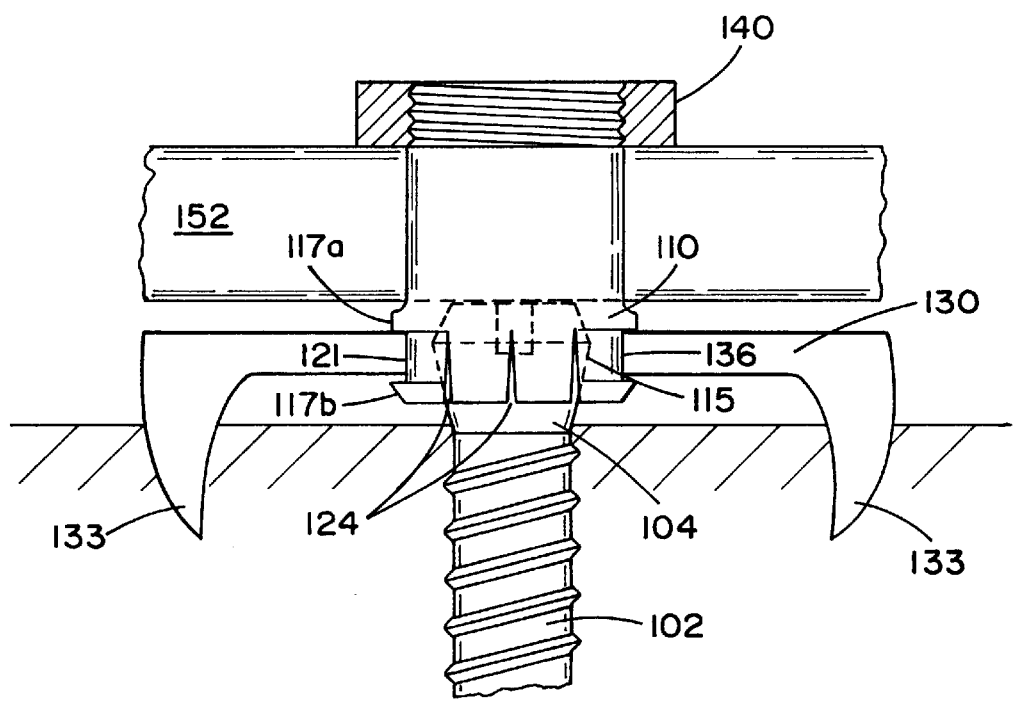
FIG. 7 is a side cross section view of a fully assembled embodiment of the present invention.

Referring now to FIG. 7, a completely assembled embodiment of the present invention is provided in a side cross section view, this view being taken along a direction in which the rod receiving member 110 is rotated about its elongate axis by 90 degrees from the orientation illustrated in FIG. 4. The implantation of this device, as well as its functionality and advantages shall be explained in conjunction with the description of the elements and workings set forth in this FIG. 7. The rod receiving member 110 is inserted into the hole 134 of the staple 130, such that the rim 136 of the hole 134 is mounted around the annular recess 119 of the member and each can rotate independently. The screw 100 is then advanced into the rod receiving member 110 until the tapered surface of the head seats loosely against the bearing surface 115 of the interior side wall of the member 110. In this initial incarcerated state, the screw 100 and the member 110 and the staple 130 all remain rotationally independent about the common elongate axis.

The screw is then driven into the vertebral bone until the barbs 133 of the staple begin to dig into the surface of the bone also. The screw and staple are each advanced further until both are sufficiently embedded into the bone as to ensure secure fixation. In this configuration, the top surface of the head 104 of the screw 100 is disposed above the lowermost surface of the rod receiving channel 116. The rod receiving member 110 is then independently rotated into the appropriate orientation for receiving the rod 152. Once the staple 130, rod receiving member 110, and screw 100 have been properly positioned, the rod 152 is inserted into the rod receiving channel 116, and seats against the upper surface of the head 104 of the screw 100. The subsequent application of the top locking nut 140 onto the threading 118 of the upwardly extending arms 113a.113b, and it's advancement downwardly, causes several simultaneous events to take place. First, the rod is compressed between nut and the head of the screw, thereby locking the rod to the screw and the rod receiving member. Second, the rod receiving member 110 is drawn upwardly by the continued tightening of the nut 140 causing the head 104 of the screw 100 to be driven downwardly in the axial bore 111 of the member which causes the side walls of the lower portion 114 of the member to expand outwardly, locking the member to the staple 130. Third, and correspondingly, the head of the screw, which was previously loosely incarcerated within the axial bore 111, is locked securely within the member 110 by a compression lock of the inner bearing surface 115 of the bore 111 against the head 104. Thus the staple 130, the rod 152, the screw 100, the rod receiving member 110, and the vertebral bone 150 are stably fixed together. This assembly strongly prevents screw pullout failure of the rod immobilization construct by providing a wider base of fixation strength for anchoring to the bone, as well as providing selective rotational freedom for the surgeon to align the rod with the channel, without risking a poor staple to screw interface.

While there have been described and illustrated embodiments of a rod, vertebral body screw and staple assembly for use with anterior or lateral spinal rod implantation apparatus, it will be apparent to those skilled in the art that variations and modifications are possible without deviating from the broad spirit and principle of the present invention. The present invention shall, therefore, be limited solely by the scope of the claims appended hereto.

We claim:

1. A vertebral body screw and staple assembly for use with orthopedic rod implantation apparatus, comprising:

a vertebral body staple having first and second portions thereof, said first portion including means for direct fixation of the staple to vertebral bone, said second portion having a throughhole formed therein, said throughhole having an interior sidewall;

a vertebral body screw having a shaft which is insertable into a vertebral bone and a head portion which includes a tapered portion;

a rod receiving member including an upper portion, a lower portion, and an axial bore,
said upper portion including a rod receiving channel,
said lower portion including at least one slot formed therein such that said lower portion is expandable upon the application of a radial force from within the bore, and
said bore including a tapered interior bearing surface;

means for securing a rod in said rod receiving channel;

said throughhole of said staple being mountable about the lower portion of said rod receiving member, such that mounting of the staple about the lower portion of the member, the insertion of said screw through said bore of said rod receiving member, insertion of the screw into the vertebral bone, the insertion of a rod in said rod receiving channel, and the application of said means for securing the rod in the rod receiving channel, causes the head of the screw to be driven against the tapered axial portion of the bore, the expanding of the lower portion of the rod receiving member, the locking the staple to the rod receiving member, and the locking of the screw head within the axial bore, thereby fully securing the assembly to the vertebral bone.

2. The vertebral body screw and staple assembly as set forth in claim 1, wherein said means for direct fixation of the staple to vertebral bone comprises a plurality of downwardly extending barbs.

3. The vertebral body screw and staple assembly as set forth in claim 1, wherein the lower portion of the rod receiving member further includes an exterior annular recess into which the interior sidewall of the staple throughhole seats.

4. The vertebral body screw and staple assembly as set forth in claim 1, wherein said means for securing a rod in said rod receiving channel comprises a top locking nut which mates to a threading formed on the upper portion of the rod receiving member.

5. A vertebral body screw and staple assembly for use with orthopedic rod implantation apparatus, comprising:

a vertebral body staple having a portion thereof which is flat, said flat portion having an upper surface and a lower surface, said staple further having a plurality of vertebral bone fixation protuberances extending downwardly therefrom, said flat portion further including a throughhole formed therein which extends from the upper surface through the lower surface, said throughhole having an annular rim;

first means for securing a rod in a rod receiving channel;

a vertebral body screw having a shaft portion and a tapered head portion a rod receiving member having an upper portion, a lower portion, and an axial bore,
- said upper portion having a rod receiving channel formed therein which has a lower channel surface and second means formed thereon for receiving thereon said first means for securing said rod in said rod receiving channel,
- said axial bore having an inwardly directed tapered bearing surface at the lower end thereof for receiving thereon the tapered head of said screw such that the screw and the rod receiving member may initially rotate freely relative to one another with the head of the screw extending above the lower channel surface of he rod receiving channel, and
- said lower portion of said rod receiving member having an exterior surface including at 5 least one slot formed therein such that the lower portion is expandable by the application of an outwardly directed radial force against the tapered bearing surface of the axial bore, said lower portion being at least partially insertable through said throughhole of said staple such that said annular rim of said throughhole seats against the exterior surface of the lower portion such that the staple and the rod receiving member may initially rotate freely relative to one another;

whereby the mounting of the staple about the exterior surface of the lower portion of the rod receiving member, the insertion of the screw through the axial bore of the rod receiving member, the insertion of the screw into a vertebral bone, the placement of the rod into the rod receiving channel and onto the head of the screw head, and the application of the first means of securing the rod in the rod receiving channel causes the screw to advance into the bore, causing the lower portion of the rod receiving member to expand and lock to the staple, the head of the screw to lock to the rod and to the rod receiving member, and therefore the entire assembly to be locked together in a fully secured combination which is fixed to the vertebral bone.

6. The vertebral body screw and staple assembly as set forth in claim 5, wherein the lower portion of the rod receiving member further includes an exterior annular recess into which the interior sidewall of the staple throughhole seats.

7. A vertebral body screw and staple assembly for use with orthopedic rod implantation apparatus, comprising:

a vertebral body staple having a throughhole formed in a flat surface thereof, the throughhole having a rim;

a vertebral body screw having a shaft and a cylindrical tapered head portion, a rod receiving member having a tapered axial bore for receiving the head of the screw, a rod receiving channel, and a slotted lower portion which is expandable upon the application of a radial force applied thereto; and means for securing a rod in said rod receiving channel, said screw being positionable within the bore of the rod receiving member and the staple being mountable about the lower portion of the rod receiving member, such that the insertion and locking of a rod into the rod receiving channel causes the head of the screw to be driven into the axial bore and causes the lower portion of the rod receiving member to expand, thus locking the screw, the rod receiving member, the staple, and the rod together in a fully secured combination.

* * * * *